United States Patent
Miller et al.

(10) Patent No.: US 7,863,307 B2
(45) Date of Patent: *Jan. 4, 2011

(54) PROCESS FOR SYNTHESIZING A CETP INHIBITOR

(76) Inventors: Ross A. Miller, Merck & Co., Inc. P.O. Box 2000, Rahway, NJ (US) 07065-0907; Aaron S. Cote, Merck & Co., Inc. P.O. Box 2000, Rahway, NJ (US) 07065-0907

( * ) Notice: Subject to any disclaimer, the term of this patent is extended or adjusted under 35 U.S.C. 154(b) by 278 days.

This patent is subject to a terminal disclaimer.

(21) Appl. No.: 11/922,905

(22) PCT Filed: Jun. 29, 2006

(86) PCT No.: PCT/US2006/025511

§ 371 (c)(1), (2), (4) Date: Dec. 21, 2007

(87) PCT Pub. No.: WO2007/005572

PCT Pub. Date: Jan. 11, 2007

(65) Prior Publication Data

US 2010/0041724 A1 Feb. 18, 2010

Related U.S. Application Data

(60) Provisional application No. 60/696,233, filed on Jul. 1, 2005.

(51) Int. Cl.
*A61K 31/421* (2006.01)
*C07D 263/20* (2006.01)
(52) U.S. Cl. ...................................... 514/376; 548/229
(58) Field of Classification Search ................ 514/376; 548/229
See application file for complete search history.

(56) References Cited

FOREIGN PATENT DOCUMENTS

| WO | WO 2006/014357 | 2/2006 |
|---|---|---|
| WO | WO 2006/014413 | 2/2006 |

OTHER PUBLICATIONS

Okamoto et al. Nature Jul. 13, 2000, 406, 203-207.*
Schafer et al. (Drug Discovery Today 2008, 13 (21/22), 913-916).*
Horig et al. Journal of Translational Medicine 2004, 2(44).*

* cited by examiner

*Primary Examiner*—Jason M Nolan
(74) *Attorney, Agent, or Firm*—Mark R. Daniel; James L. McGinnis

(57) ABSTRACT

An efficient process is disclosed for producing a compound that is an inhibitor of CETP. The last step of the process is the coupling of an oxazolidinone derivative with a biphenyl moiety to provide a compound of formula (I). In a specific embodiment of this synthesis, a crystalline product is produced which is characterized as a non-solvated crystalline polymorph.

24 Claims, 10 Drawing Sheets

PROCESS FOR SYNTHESIZING A CETP INHIBITOR

CROSS REFERENCE TO RELATED APPLICATIONS

This application is a U.S. National Phase application under 35 U.S.C. §371 of PCT Application No. PCT/US2006/025511, filed Jun. 29, 2006, which claims priority under 35 U.S.C. §119(e) from U.S. Application No. 60/696,233, filed Jul. 1, 2005.

FIELD OF THE INVENTION

This invention relates to a process for synthesizing a chemical compound that inhibits cholesterol ester transfer protein (CETP) and to crystalline polymorphic forms of a particular compound made by this process. The product of the process raises HDL-cholesterol in mammals and is expected to have utility in the treatment and/or prevention of atherosclerosis and in delaying the advancement of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as the average age of the population increases and as an epidemic in obesity and diabetes continues to grow.

Inhibition of CETP is a promising new approach to reducing the incidence of atherosclerosis. Statins have been important in reducing the incidence of CHD by reducing LDL-cholesterol (the "bad cholesterol"), but are relatively ineffective at raising HDL-cholesterol ("the good cholesterol"). CETP inhibitors raise HDL-cholesterol, and may provide a potent new tool for reducing CHD and atherosclerosis in the general population. Administration of both a CETP inhibitor and a statin may be especially valuable for treating and preventing atherosclerosis. Pharmaceuticals containing CETP inhibitors are not currently available. Pfizer's torcetrapib is a CETP inhibitor that is currently in Phase III trials.

SUMMARY OF THE INVENTION

The present invention provides a process for preparing compounds having formula I. These novel compounds are potent CETP inhibitors:

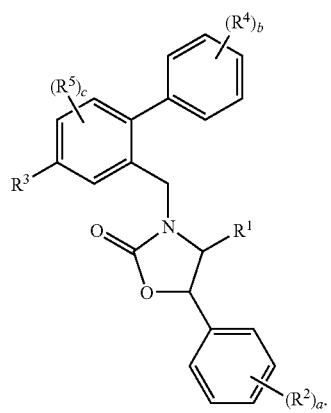

The process provides a convergent synthesis of Compound I. The complete process comprises the synthesis of two key intermediates, II and III. The key intermediates are then coupled in the last step of the process, which is shown below:

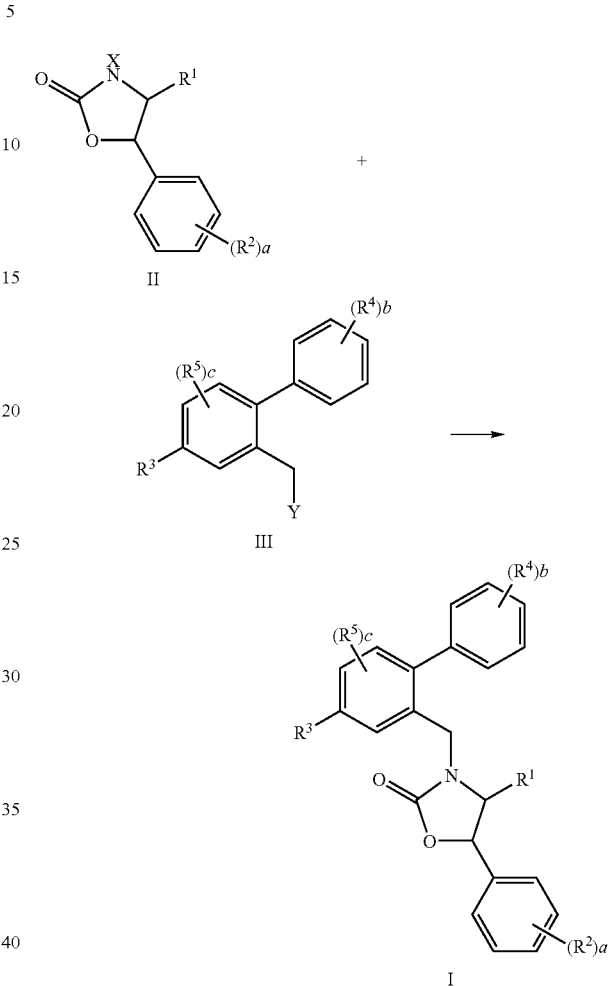

In the compounds having Formula I, II and III, $R^1$ is H or $C_{1-4}$alkyl, which is optionally substituted with 1-5 F groups;

$R^2$, $R^4$, and $R^5$ are each independently selected from the group consisting of halogen, $C_{1-4}$alkyl, and —$OC_{1-4}$alkyl, wherein $C_{1-4}$alkyl and —$OC_{1-4}$alkyl are optionally substituted with 1-5 halogens;

$R^3$ is selected from H, halogen, $C_{1-4}$alkyl, and —$OC_{1-4}$alkyl, wherein $C_{1-4}$alkyl and —$OC_{1-4}$alkyl are optionally substituted with 1-5 halogens;

a and b are each independently selected from integers from 1-4;

c is an integer from 0-2;

X is H or a group I metal cation (e.g. Na, K, Li, or Cs), and Y is a leaving group (i.e. a group that is easily displaced). Examples of leaving groups include halogen, $C_{1-3}$ alkanoate (e.g. acetate), trifluoroacetate, and triflate.

When X is H, a base is also included in the reaction, where the base is an alkali metal salt of a strong base. The alkali metal may be Na, K, Li, or Cs; and in subgroups, the alkali metal may be Na or K; in other subgroups, the alkali metal may be Na; in other subgroups, the alkali metal may be K. Examples of alkali metal salts of strong bases include sodium amide, potassium amide, NaHMDS, KHMDS, n-butyl lithium, and t-butyl lithium. The use of the base yields as an intermediate compound II, with X being Na, K, Li, or Cs.

In embodiments of the reaction described above, $R^1$ is H or $C_{1-3}$ alkyl, optionally substituted with 1-5 F. $R^1$ in other embodiments is $C_{1-2}$ alkyl, optionally substituted with 1-3 F. In preferred embodiments, $R^1$ is $CH_3$.

In embodiments of the reaction, $R^2$, $R^4$ and $R^5$ are each independently F, $C_{1-3}$ alkyl optionally substituted with 1-5 F, or —$OC_{1-3}$ alkyl optionally substituted with 1-5 F. In other embodiments, $R^2$, $R^4$, and $R^5$ are each independently F, $C_{1-3}$ alkyl, optionally substituted with 1-5 F, or —$OC_{1-2}$ alkyl, optionally substituted with 1-5F. In other embodiments, $R^2$, $R^4$, and $R^5$ are each independently selected from $C_{1-3}$ alkyl, $CF_3$, —$OCH_3$, —$OCF_3$, and F.

In other embodiments, each $R^2$ is $CH_3$ or $CF_3$.

In other embodiments, $R^2$ is $CF_3$.

In other embodiments, $R^3$ is $C_{1-3}$ alkyl, —$OC_{1-3}$ alkyl, or F, wherein $C_{1-3}$ alkyl and $OC_{1-3}$ alkyl are optionally substituted with 1-5 F.

In other embodiments, $R^3$ is $CH_3$, $CF_3$ or F.

In other embodiments, $R^3$ is $CF_3$.

In some embodiments, a is 1 or 2, and in other embodiments, a is 2.

In some embodiments, b is 1-3. In other embodiments, b is 2 or 3. In other embodiments, b is 3.

In some embodiments c is 0 or 1. In other embodiments, c is 0.

In some embodiments, X is H, Na, or K. In other embodiments, X is Na or K.

In some embodiments, Y is halogen. In other embodiments Y is Cl, Br or I. In other embodiments, Y is Cl or Br. In other embodiments, Y is Cl.

Unless otherwise stated, alkyl groups may be either linear or branched.

DETAILED DESCRIPTION OF THE INVENTION

Figure 1:
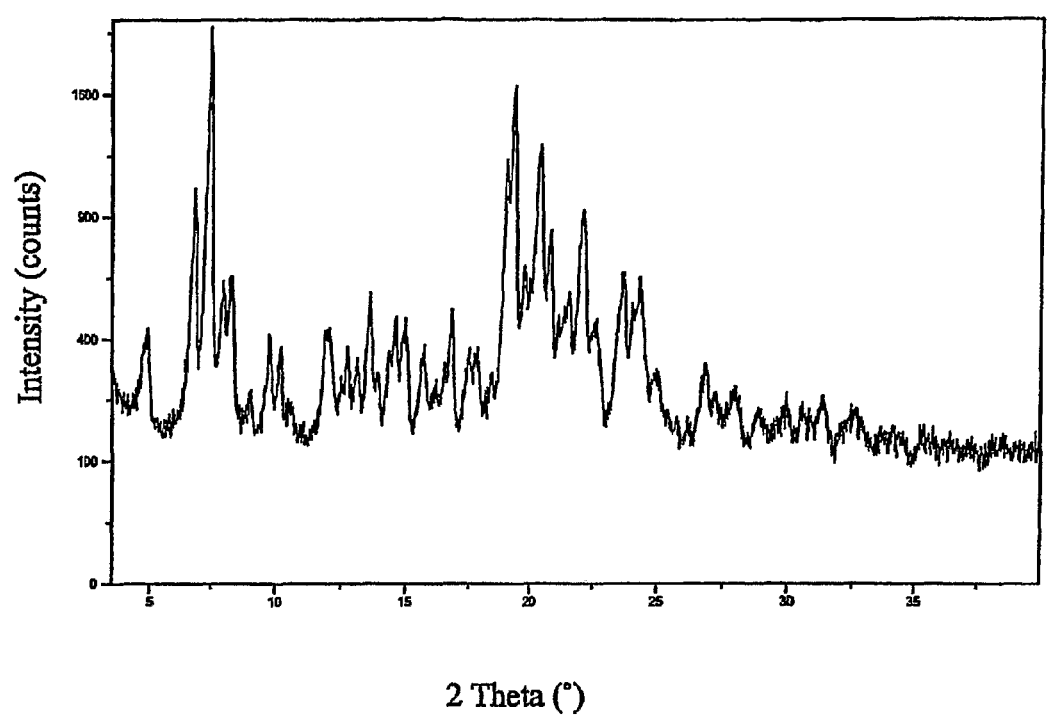
FIG. 1 is a characteristic X-ray powder diffraction pattern of the crystalline non-solvate form of compound 12.

Further embodiments are described below:

In Intermediate II, X is H or a group I alkali metal (e.g. Na, K, Li, or Cs). The group I metal cation may be complexed with a ligand, such as TMEDA, or with an ether or polyether, such as a crown ether, that increases the reactivity of the negatively charged N of the oxazolidinone group of II. X may also be H. When X is a metal cation (e.g. Na, K, Li, or Cs), Intermediate II can be made by the reaction of the oxazolidinone (X is H) with a metal hydride, an alkyl metal compound, or a reactive alkali metal amide. Examples include the reaction of the oxazolidinone (X=H) with bases such as sodium amide, potassium amide, NaHMDS, KHMDS, n-butyl lithium, and t-butyl lithium. When X is H, a base is also included in the reaction, where the base is one of the bases that are used to convert the oxazolidinone to reactive compounds in which X is Na, K, Li, or Cs. The X groups are selected from K and Na in many embodiments. The group X in Example 1 is Na.

In Intermediate III, Y is a leaving group (i.e. a group that is easily displaced). The leaving group is usually anionic after it has been displaced. The most common leaving groups are halogens, such as Cl, Br, I or F. The leaving may also be the deprotonated form of an organic acid, such as triflate or trifluoroacetate. In many embodiments, the leaving group Y is selected from Br, Cl and I. In many embodiments, the leaving group Y is selected from Br and Cl. The group Y is Cl for the synthesis of compound 12 in Example 1.

In the reaction described above, Intermediate II often will be charged to the reaction vessel as the neutral oxazolidinone (X=H), then converted to the alkali metal salt, where X is an alkali metal, and then reacted with Intermediate III without being isolated. For purposes of this application, this is the reaction of the alkali metal salt of the oxazolidinone (X is an alkali metal) with Intermediate III, even though the oxazolidinone (X is H) is the starting material that is charged to the reaction vessel. Alternatively, Intermediates II and III may be charged to the reaction vessel first, and if X is H, then enough base is added to bring about the coupling reaction. This is also the reaction of the oxazolidinone in which X is an alkali metal with Intermediate III.

The reaction is generally carried out in a polar aprotic solvent, such as HMPA, DMF, or DMAC. In many embodiments, DMF is used as the solvent. The reaction proceeds under mild conditions of temperature. Exemplary mild conditions are −20° C., −10° C., 0° C., 10° C., 20° C., 30° C. and 40° C. The reaction, and particularly the deprotonation of the oxazolidinone with a base, is often started by adding the base at reduced temperature (e.g. −20° C., −10° C., or 0° C.), and then warming the mixture to room temperature.

In a preferred embodiment, compound I has the structure of formula 12:

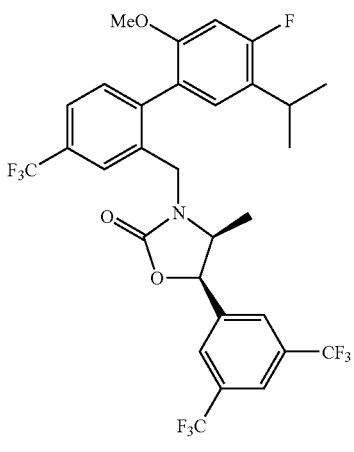

12 and is made by the reaction of compounds II and 7, shown below:

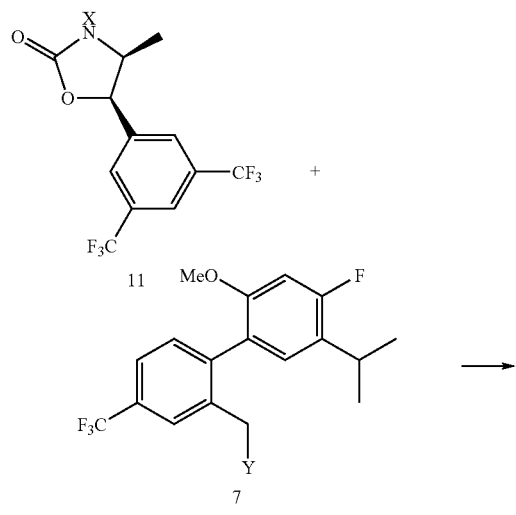

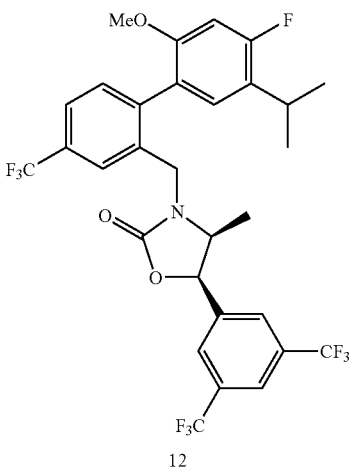

12

The complete synthesis of 12 is shown in Example 1. In compound II in Example 1, X is Na, which is made without isolation from the neutral oxazolidinone (X=H), and is reacted without isolation with Intermediate 7, in which Y is Cl. The example is provided to further illustrate the invention and should not be treated as limiting the invention in any way. The scope of the invention is defined by the claims.

Example 1

The complete process for synthesizing compound 12 (formula I) is summarized in Scheme I, and is subsequently disclosed in detail, step by step. In this process as shown below, the group X is H, which is converted to sodium in an unisolated intermediate, which undergoes the coupling reaction, and the group Y is Cl.

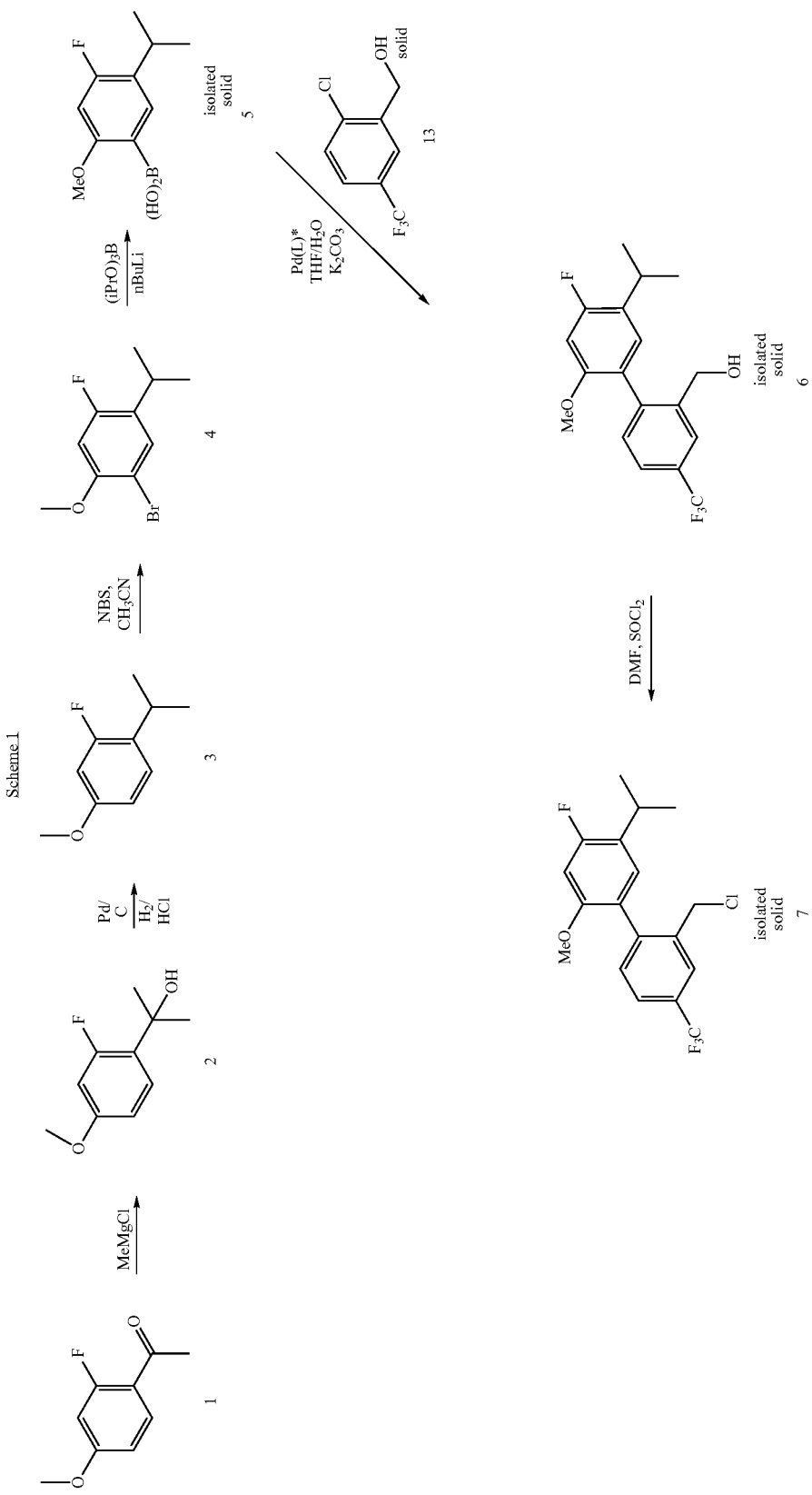

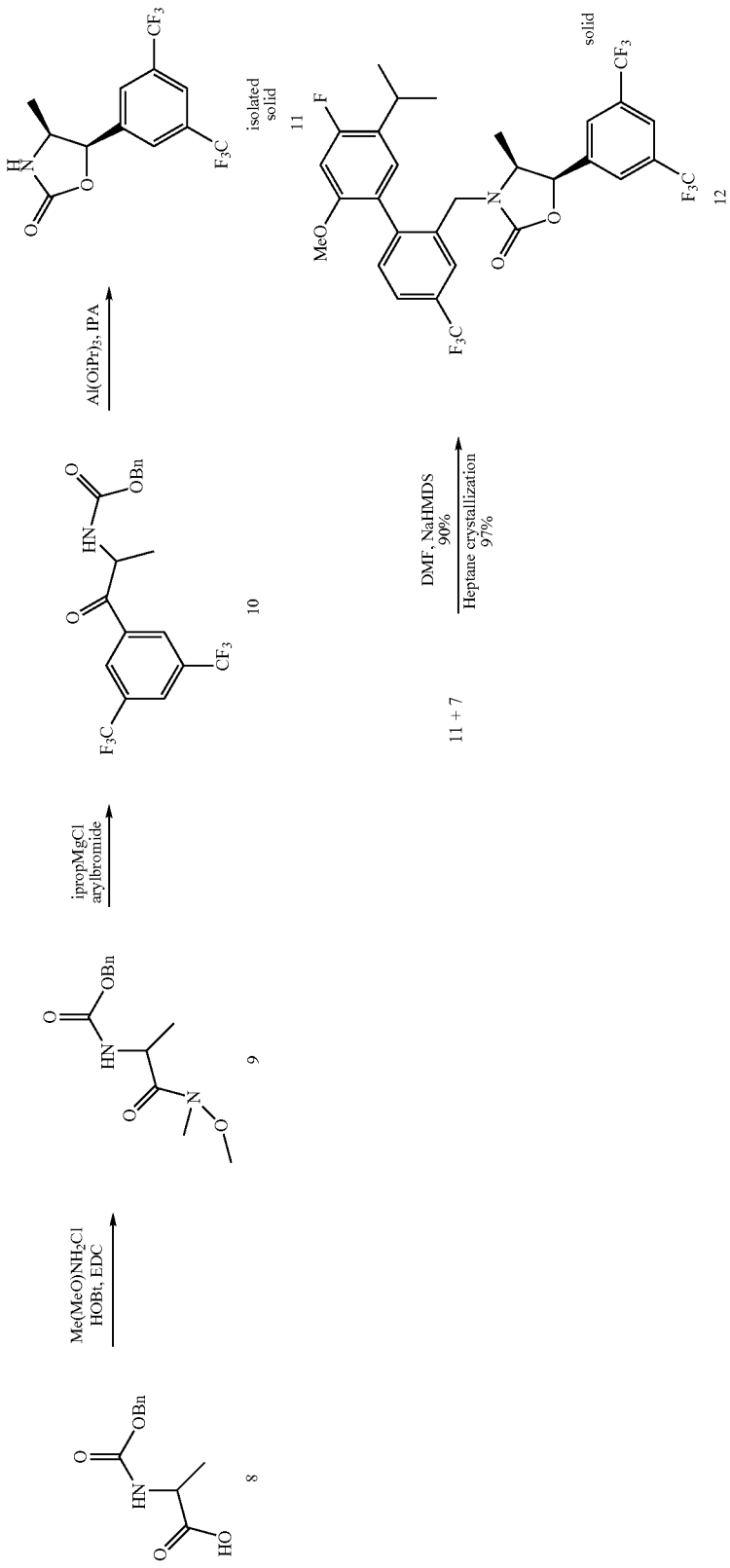

DEFINITIONS

The terms used throughout this application, and particularly in the examples, are generally well known to chemists who work in the area of process research. Some of these are also defined below:

"EDC" is 1-ethyl-3-(3-dimethylaminopropyl)carbodiimide.

"DIPEA" is diisopropylethylamine.

"DMAC" is dimethylacetamide.

"DMSO" is dimethylsulfoxide.

"DMF" is dimethylformamide.

"Halogen" includes fluorine, chlorine, bromine and iodine.

"HMPA" is hexamethylphosphoric triamide.

"HOBT" is 1-Hydroxybenzotriazole.

"IPAC" is isopropyl acetate.

"Me" represents methyl.

"NaHMDS" is sodium hexamethyldisilazide.

"TMEDA" is tetramethylethylenediamine.

"Weinreb amine" is N,O-dimethylhydroxylamine.

Synthesis of Intermediate 7

Intermediate 7 is made in 6 steps from readily available materials. The synthesis is summarized below as a 4-step synthesis of the boronic acid intermediate 5, which is isolated as a solid material. The boronic acid is then carried on in two more steps to the key intermediate 7, which is also isolated as a solid product.

The boronic acid intermediate is synthesized in 4 steps as shown below, and as summarized in Scheme 2.

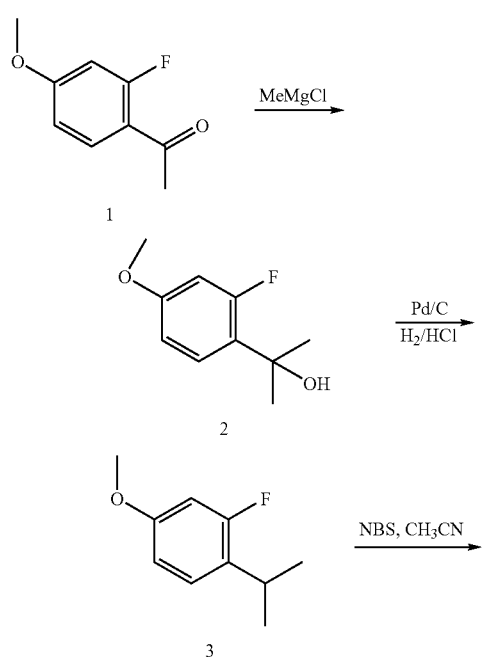

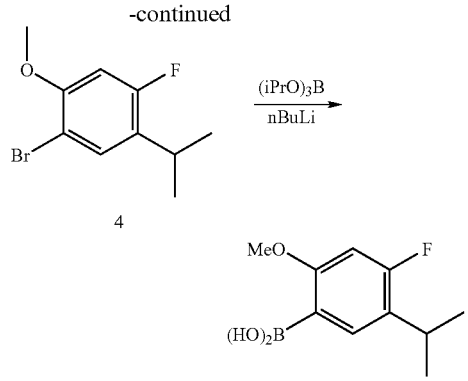

Conversion of 1 to 2:

THF (24 L) was added to a 100 L cylindrical vessel at room temperature. To this was added 2.75 kg of CeCl₃. The resultant slurry was aged at room temperature for 1.5 hours. A sample was then examined under a microscope to confirm that the desired form change had occurred. The slurry was cooled to 9° C. and MeMgCl was added. The rate of addition was adjusted to maintain internal temperature below 19° C. The mixture was cooled to −11° C., and a solution of acetophenone 1 (4.0 kg diluted to 10 L with THF) was added dropwise, maintaining the internal temperature below 0° C. The reaction mixture was then aged at a temperature below 0° C. for an hour. The reaction was quenched with 5.7 L of 3N HCl in a dropwise fashion, maintaining the internal temperature below 15° C. The quenched reaction mixture was then aged at 5-10° C. for 1.5 hours and was filtered through a plug of Solka Floc.

Hydrogenation of 2 to 3:

The THF solution of 2 was solvent switched into ethanol (~18 L volume), and 1.9 L HCl was added, followed by 190 gm of 10% Pd/C (50% water). The mixture was placed under 15 psi hydrogen at 40° C. until the reaction was complete based on HPLC analysis. The mixture was cooled to room temperature. The catalyst was removed by filtration using Solka-Flok as a filter aid. The anisole product in ethanol was then solvent switched into acetonitrile for the next step.

Bromination of 3 to 4:

Anisole 3 is diluted in acetonitrile (1.72 L, 4 mL MeCN/mMol 3). This mixture is warmed to 35° C., and NBS (1.1 eq, 84 g) is added in a single solid addition. The reaction is maintained at 35° C. and is complete in 2-4 hours. The solution is concentrated to 400 mL total volume and diluted with 1 L of toluene. The solution is then washed with sodium thiosulfate and water to remove the succinimide by-product. The organic layer is then concentrated and solvent switched to toluene.

Conversion of Aryl Bromide 4 to Boronic Acid 5:

A 75 L glass reaction vessel was charged with 1.87 kg of aryl bromide 4 (7.6 Mol), which was added as 6.4 kg of a 29.1 wt % solution of 4 in toluene. This solution was diluted with 5.6 L of THF. The vessel was flushed with nitrogen, and tri-isopropylborate (1.35 eq, 2.35 L, 10.3 Mol) was added. The mixture was cooled to <−70° C. Then 5.9 L of 1.6 M n-BuLi in hexanes (9.5 Mol) was added slowly over 4 hours, maintaining a temperature of <−55° C. Thirty minutes after completion of the n-BuLi addition, the reaction was complete by LC analysis. The reaction was warmed to −35° C. and quenched into 3.0 M $H_2SO_4$ solution (5.6 L). The aqueous phase after the quench should be acidic (pH~2). MTBE (7.5 L) was added to the mixture to dilute the organic layer. The mixture was stirred (15 min) and the aqueous layer was cut away. The organic layer was washed with another 5.6 L of a 3.0 M $H_2SO_4$ solution (15 min). After separating layers again, the organic MTBE/Toluene layer was extracted twice with 1 M KOH (15.1 L first and then 7.6 L). The two KOH extractions were combined, diluted with 2-propanol (6.4 L), and cooled to 15° C. Then the solution was slowly acidified to pH~2 using 3.0 M sulphuric acid (~7.6 L) while maintaining temperature at 15-20° C. The resulting slurry was stirred for 1 h and then filtered. The filter cake was washed with water (2×6 L) and dried under an air flow for 1 day. The filtered solid was placed in an oven under vacuum at 50° C. for 2-3 days to decompose a diaryl impurity and to dry the solid. The off-white crystalline solid was isolated to yield boronic acid 5.

Boronic acid 5 is then converted to the biaryl intermediate 7 in 2 steps, which are summarized in Scheme 3 below and are described in detail in the subsequent procedures.

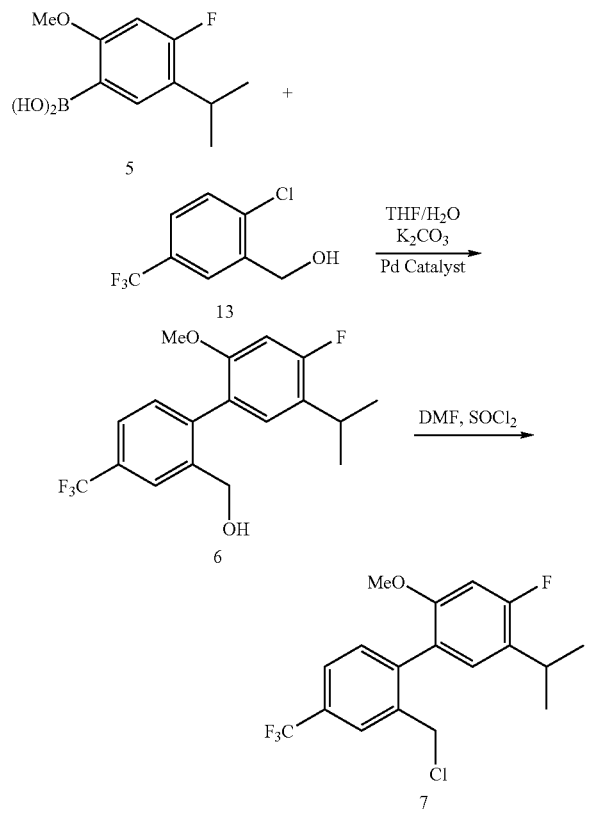

Scheme 3

Step 1: Suzuki Coupling Reaction of Boronic Acid 5 and Aryl Chloride 13 to Yield 6:

A 3 M $K_2CO_3$ solution is prepared by adding 4.71 kg of solid $K_2CO_3$ to 10.3 L water. Cooling is applied to keep the solution at 20-25° C. THF (12 L), aryl chloride 13 (2.69 kg), and boronic acid 5 (2.74 kg) are added to the $K_2CO_3$ followed by a 1 L THF rinse. HPLC analysis is used to confirm the 1.00/1.00 ratio of 5/13. The solution is degassed by sparging with nitrogen gas for 70 min. The catalyst, 1,1 bis(di-tert-butylphosphino)ferrocene palladium dichloride (42 g) is added as a solid and is followed by a degassed THF rinse (1.5 L). The organic layer turns dark brown immediately. The biphasic mixture is aged at 36-40° C. with vigorous stirring. After HPLC reveals complete conversion (15-18 h), the mixture is cooled to rt and the aqueous layer is removed. To the organic layer is added heptane (25.6 L) and water (25.6 L) and the layers are cut. The organic layer is washed with water (19 L). The organic layer is treated with 680 g Darco KB-B at rt for 60 min and filtered through solka-floc with a 10% THF/Heptane rinse (~15 L). The solvent is switched to heptane (~35 L) at ~45-50° C. until <0.5 v % of THF is left. More heptane is added to bring the total volume to ~45-50 L. The solution is seeded with crystals obtained from earlier runs if no seed bed forms. The slurry is slowly cooled to rt and then to −15° C. After aging at −15° C. for 1-2 h, after LC of the supernatant shows that there will be ~2 g/l loss of the product in the supernatant, the slurry is filtered and the product is washed with cold heptane (~25 L), providing compound 6.

Step 2: Chlorination of 6 to 7:

To a solution of biaryl compound 6 (3.4 kg) in DMF (17 L) which was maintained at 10° C. was added thionyl chloride (940 ml), and then the mixture was warmed to room temperature. The mixture was aged until >99.8% conversion was measured by HPLC. Water (3.4 L) was then added. Seed crystals obtained from earlier batches (1 wt %) were added, and the mixture was aged for 30 min more before slowly adding 5.1 L of additional water over ~1 hr. The solid was filtered and washed with first 20 L 1:1 DMF:water and then 3×20 L water. The solid product 7 was dried at 20° C. until <0.1 wt % water remained.

Chiral Synthesis of (4S,5R)-5-[3,5-Bis(trifluoromethyl)phenyl]-4-methyl-1,3-oxazolidin-2-one (11)

The oxazolidinone intermediate 11 is made directly from the chiral starting material CBZ-L-alanine (8) by the 3-step route shown below. The enantiomer of this compound (4R, 5S)-5-[3,5-bis(trifluoromethyl)phenyl]-4-methyl-1,3-oxazolidin-2-one can be made by an analogous route starting from CBZ-D-alanine.

Step 1: Conversion of 8 to 9:

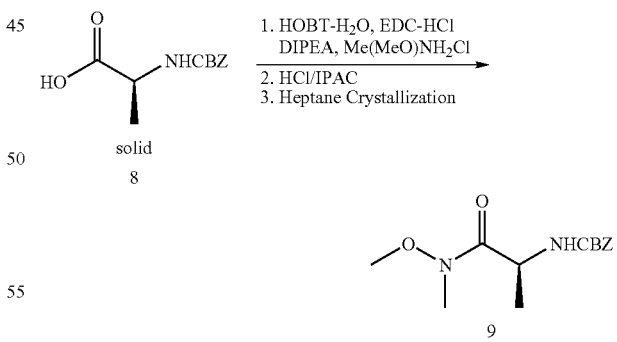

CBZ-L-Alanine (6.5 kg, 28.5 mol), HOBT-hydrate (4.8 kg, 34.8 mol), Weinreb amine-HCl salt (3.4 kg, 36.2 mol) and THF (32 L) are charged to a clean flask under nitrogen. The mixture is cooled to 0-10° C. and then DIPEA (12.4 L) is slowly added at a temperature less than 25° C. EDC-HCl (7 Kg, 36.2 mol) is then added slowly with cooling at 15°-25° C. The slurry is aged overnight at 20°-25° C. The mixture is then cooled to 0°-10° C., and 3 N HCl (12 L) is added slowly. Then IPAC (32 L) is added and the layers are separated. The organic layer is washed once with HCl (13 L) and twice with 8% NaHCO3 (13 L) (CAUTION: FOAMING). The organic layer is then concentrated under vacuum to about 15 L at 50° C. The clear solution is cooled slowly to room temperature, allowing the product to crystallize. Heptane (~70 L) is then added slowly. The slurry is filtered, washed with heptane (18 L), and dried at room temperature on the filter pot. Product is obtained with >99.9% ee measured by chiral HPLC.

Step 2: Conversion of 9 to 10

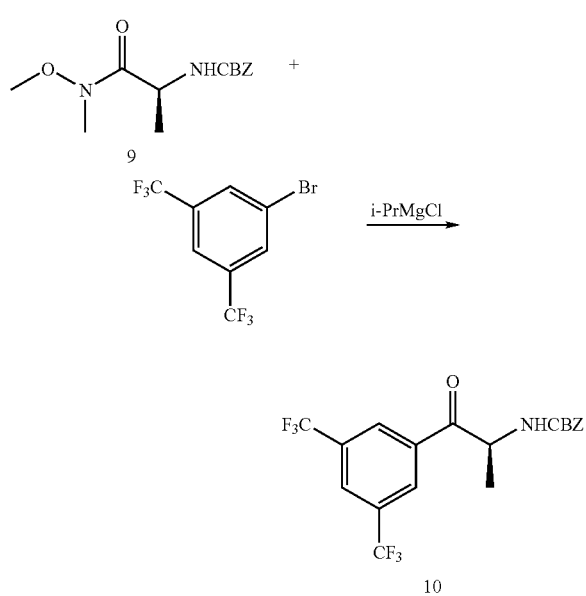

The Weinreb amide 9 from the previous step (6 kg, 22.5 mol) and 3,5-bis(trifluoromethyl)bromobenzene (4.85 L, 28.1 mol) are dissolved in anhydrous THF (24 L). The solution is purged with nitrogen to remove oxygen. The water content should be <500 ppm at this point. Atmospheric distillation can be carried out to azeotropically remove water if necessary. The solution is cooled to −10° C. and iso-PrMgCl in THF (56.4 mol) is slowly added (2 hours) to the reaction via addition funnel, maintaining a reaction temperature ≦−5° C. The solution is allowed to warm to 20° C. and aged overnight at 20° C., until the amide is <0.5 LCAP. The reaction is then cooled to −10° C. under nitrogen and is quenched slowly over 2 hours into 5N HCl (14 L) that is maintained at 0-5° C. MTBE (12 L) is added and the biphasic mixture is agitated for 5 min. After warming to 20°-25° C., it is allowed to settle for 30 min, and then the layers are separated. The organic layer is washed with water twice (12 L).

The organic layer is vacuum transferred through a 1-micron in-line PTFE filter into a distillation flask and is then concentrated to ~12 L under vacuum (internal temperature <40° C.) to a minimum agitated volume. The solution is then azeotropically dried with toluene and taken to a minimum agitated volume again. The solution containing ketone 10 is used directly in the next step.

Step 3: Reduction of Ketone 10 to Chiral Oxazolidinone 11:

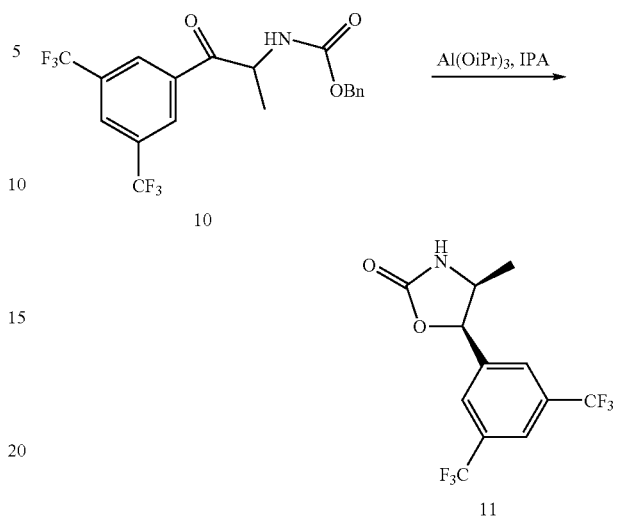

The ketone 10 (6 kg) is heated at 50° C. with 0.3 eq of Al(O-i-Pr)$_3$ (790 g) in 12 L IPA and 18 L of toluene for 15.5 hours. The solution is cooled to ambient temperature, and solid KOH pellets (1.35 kg) are added slowly with vigorous stirring, while keeping the temperature at <25° C. After about 2 hours, when HPLC shows >99.5% cyclization, 33 L of 1N HCl solution is added to quench the reaction, which is kept at <25° C. If a rag layer of solids forms, it should be filtered off. The rag layer is racemic oxazolidinone, and removal increases the enantiomeric excess. The organic layer is then washed first with 36 L of 0.5N HCl, then with 6 L IPA combined with 45 L water, and finally with 6 L IPA combined with 36 L water. The organic layer is transferred via an inline filter. The solvent is switched to heptane (target volume is ~42 L) at ~40° C. until <2 v % toluene is left. Aging at rt for 2 h gives the solid product 11.

Alkylation of Oxazolidinone 11 with 7

Oxazolidinone 11 is alkylated with 7 to yield the desired product, (4S,5R)-5-[3,5-bis(trifluoromethyl)phenyl]-3-{[4'-fluoro-5'-isopropyl-2'-methoxy-4-(trifluoromethyl)biphenyl-2-yl]methyl}-4-methyl-1,3-oxazolidin-2-one (12):

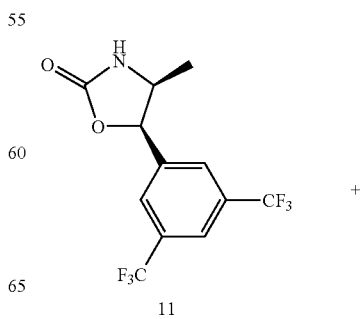

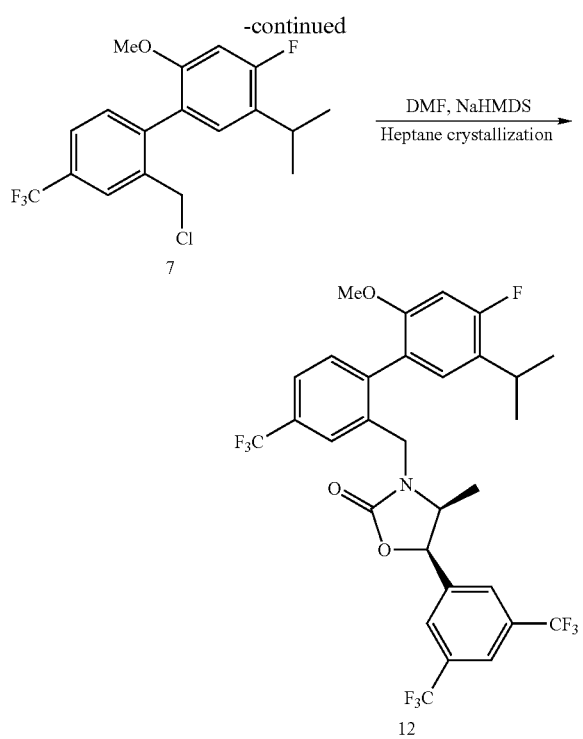

The chiral intermediate (4S,5R)-5-[3,5-Bis(trifluoromethyl)phenyl]-4-methyl-1,3-oxazolidin-2-one (11) which was made above is dissolved in DMF (2.8 kg in 32.7 L) and cooled to −15° C. 2.0 M NaHMDS (3.92 L, 1.05 eq) was then added over 1.5 hr, followed by addition of the biaryl chloride 7 (2.8 kg) in DMF. The mixture was warmed to +12° C. and was aged until complete conversion took place. Then 5N HCl (3.4 L) was added, followed by 16 L of 10% IPAC/Heptane and 34 L of water, keeping the temperature between 10° C. and 20° C. throughout. The layers were cut and the organic layer was washed twice with 14 L of 1:1 DMF:water followed by two 14 L water washes. The organic layer was assayed for yield and was then filtered through 2.4 kg of silica gel to remove the excess oxazolidinone to <0.5%. The silica was washed with 5% IPAC/Heptane. The combined organic solutions were distilled to remove IPAC to <1%. The warm heptane solution was then transferred slowly into a 20° C. heptane solution containing 10 wt % seed. The seed crystals were obtained initially from earlier batches of the same reaction. The slurry was then cooled to −20° C. and filtered. The filter cake was washed with cold heptane and was then dried, yielding 4.4 kg (88%) of the desired product 12.

Polymorphic Forms of Compound 12

Figure 2:
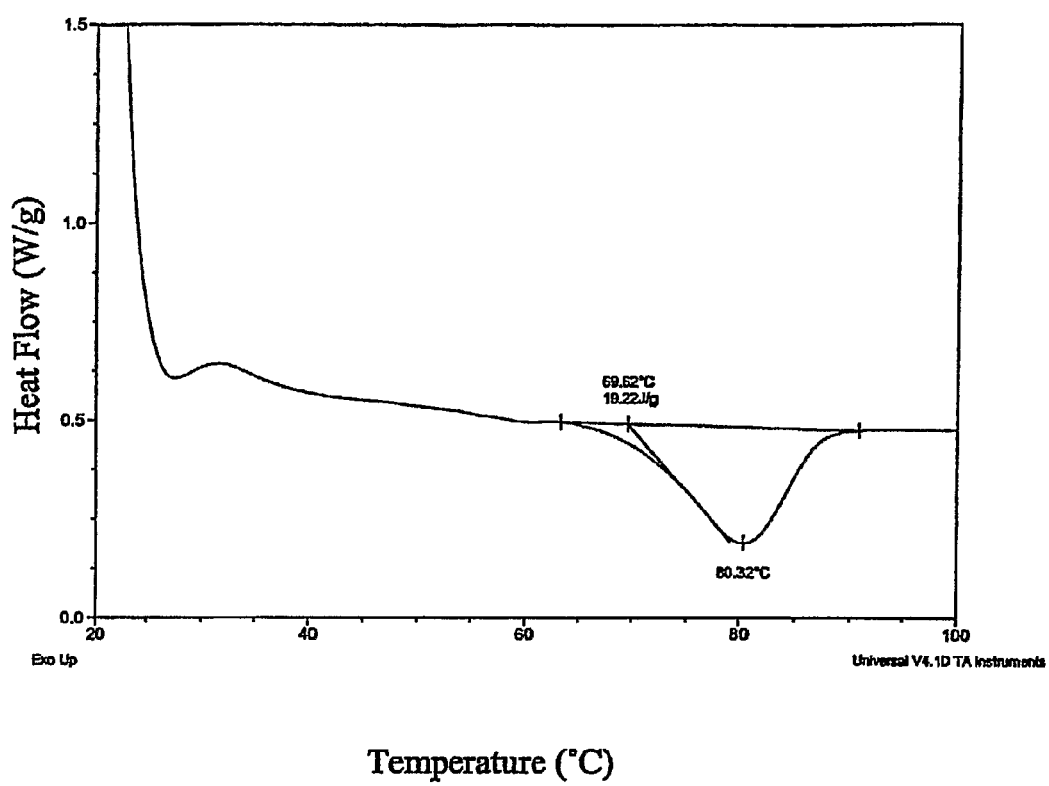
FIG. 2 is a typical DSC curve of the crystalline non-solvate form of compound 12.

The filter cake that is isolated above by filtration from heptane is initially a crystalline heptane solvate. During filtration and drying, the heptane evaporates, yielding an anhydrous non-solvated crystalline product. Heptane de-solvates at room temperature under a flow of nitrogen or air, or under vacuum. The crystalline product melts at about 69° C. (FIG. 2). The crystalline non-solvate form of compound 12 is non-hygroscopic and does not convert to a hydrate in humid or dry air. The crystalline non-solvate form of compound 12 does not convert to other crystalline forms on standing at room temperature, but slowly converts to the amorphous form on standing for long periods of time, and converts more rapidly to the amorphous form at elevated temperatures. The amorphous form of compound 12 can also be obtained from the crystalline form by milling, and from a solution in an organic solvent by spray drying or by precipitation, using water as an antisolvent.

The crystalline product 12 obtained by the process above may be used to make pharmaceutical formulations. Because compound 12 is very poorly soluble in water, it is generally beneficial to formulate compound 12 in a form that will improve its bioavailability. The crystalline product 12 can be used to make pharmaceutical formulations in which the active ingredient is changed to another form, as for example a solution, as an amorphous dispersion in a polymer, or as part of a preconcentrate that yields a microemulsion after the preconcentrate is swallowed or mixed with water. The crystalline non-solvate form of compound 12 is a useful intermediate for making these formulations because it is readily purified and handled, is non-hygroscopic, and is stable at room temperature for moderate periods of time with respect to changing to the amorphous form.

Pharmaceutical formulations that comprise compound 12 may comprise the crystalline non-solvate form of compound 12 in a detectable amount. The amount of crystalline non-solvate form of compound 12 in the solid can be quantified by the use of physical methods, such as X-ray powder diffraction (XRPD), solid-state fluorine-19 cross-polarization magic-angle spinning (CPMAS) nuclear magnetic resonance spectroscopy, solid-state carbon-13 cross-polarization magic-angle spinning (CPMAS) nuclear magnetic resonance spectroscopy, solid state Fourier-transform infrared spectroscopy, and Raman spectroscopy. Pharmaceutical formulations that comprise compound 12 may comprise about 5% to about 100% by weight of the crystalline non-solvate form of compound 12 (as a % of the amount of compound 12 in the formulation). Pharmaceutical formulations that comprise compound 12 may comprise about 10% to about 100% by weight of the crystalline non-solvate form of compound 12. Pharmaceutical formulations that comprise compound 12 may comprise about 25% to about 100% by weight of the crystalline non-solvate form of compound 12. Pharmaceutical formulations that comprise compound 12 may comprise about 50% to about 100% by weight of the crystalline non-solvate form of compound 12. Pharmaceutical formulations that comprise compound 12 may comprise about 75% to about 100% by weight of the crystalline non-solvate form of compound 12. Pharmaceutical formulations that comprise compound 12 may comprise about 100% by weight of the crystalline non-solvate form of compound 12, so that the solid Compound 12 in the formulation is substantially phase pure crystalline non-solvate form.

Pharmaceutical formulations that comprise Compound 12 may comprise Compound 12 in the crystalline non-solvate form in a detectable amount, even when the formulation is made to be non-crystalline, as for example a formulation of amorphous Compound 12, a formulation comprising an amorphous dispersion of Compound 12 in a water soluble polymer (e.g. polyvinylpyrrolidinone, a polyvinylpyrrolidinone copolymer, or a water soluble cellulosic polymer, such as HPMCAS), or a formulation comprising Compound 12 in solution, such as a microemulsion preconcentrate. The crystalline Compound 12 may be present in small amounts in these formulations for many reasons, such as because the crystalline compound is not completely changed to a non-crystalline form, or is not completely dissolved, or because Compound 12 gradually converts to the crystalline non-solvate form on standing for an extended period of time. In such pharmaceutical formulations that comprise Compound 12, the pharmaceutical formulation may comprise compound 12 in the crystalline non-solvate form in a measurable amount, which may represent at least 0.1% of the total amount of Compound 12 in the formulation; or may represent at least 0.5% of the total amount of Compound 12 in the formulation; or may represent at least 1% of the total amount of Compound 12 in the formulation; or may represent at least 5% of the total amount of Compound 12 in the formulation; or may represent at least 10% of the total amount of Compound 12 in the formulation; or may represent at least 25% of the total amount of Compound 12 in the formulation; or may represent at least 50% of the total amount of Compound 12 in the formulation.

The crystalline product is characterized below.

Characterization Methods

X-ray powder diffraction studies are widely used to characterize molecular structures, crystallinity, and polymorphism. The X-ray powder diffraction patterns are generated on a Philips Analytical X'Pert PRO X-ray Diffraction System with PW3040/60 console. A PW3373/00 ceramic Cu LEF X-ray tube K-Alpha radiation is used as the source.

In addition to X-ray powder diffraction patterns as described above, crystalline forms of compounds may further be characterized by their solid-state carbon-13 and fluorine-19 nuclear magnetic resonance (NMR) spectra. Solid-state carbon-13 NMR spectra are obtained on a Bruker DSX 400WB NMR system using a Bruker 4 mm double resonance CPMAS probe. The carbon-13 NMR spectra utilize proton/carbon-13 cross-polarization magic-angle spinning with variable-amplitude cross polarization. The samples are spun at 15.0 kHz, and a total of 1024 scans are collected with a recycle delay of 5 seconds. A line broadening of 40 Hz is applied to the spectrum before FT is performed. Chemical shifts are reported on the TMS scale using the carbonyl carbon of glycine (176.03 p.p.m.) as a secondary reference.

The solid-state carbon-13 NMR spectra are also obtained on a Bruker DSX 500WB NMR system using a Bruker 4 mm H/X/Y CPMAS probe. The carbon-13 NMR spectra utilize proton/carbon-13 cross-polarization magic-angle spinning with variable-amplitude cross polarization, total sideband suppression, and SPINAL decoupling at 100 kHz. The samples are spun at 10.0 kHz, and a total of 1024 scans are collected with a recycle delay of 5 seconds. A line broadening of 10 Hz is applied to the spectrum before FT is performed. Chemical shifts are reported on the TMS scale using the carbonyl carbon of glycine (176.03 p.p.m.) as a secondary reference.

The solid-state fluorine-19 NMR spectra are obtained on a Bruker DSX 400WB NMR system using a Bruker 4 mm CRAMPS probe. The NMR spectra utilize a simple pulse-acquire pulse program. The samples are spun at 15.0 kHz, and a total of 128 scans are collected with a recycle delay of 5 seconds. A vespel endcap is utilized to minimize fluorine background. A line broadening of 100 Hz is applied to the spectrum before FT is performed. Chemical shifts are reported using poly(tetrafluoroethylene) (Teflon®) as an external secondary reference which is assigned a chemical shift of −122 ppm.

The solid-state fluorine-19 NMR spectra are also obtained on a Bruker DSX 500WB NMR system using a Bruker 4 mm H/F/X CPMAS probe. The fluorine-19 NMR spectra utilize proton/fluorine-19 cross-polarization magic-angle spinning with variable-amplitude cross polarization, and TPPM decoupling at 62.5 kHz. The samples are spun at 15.0 kHz, and a total of 256 scans are collected with a recycle delay of 5 seconds. A line broadening of 10 Hz is applied to the spectrum before FT is performed. Chemical shifts are reported using poly(tetrafluoroethylene) (Teflon®) as an external secondary reference, which is assigned a chemical shift of −122 ppm.

DSC data are also acquired using TA Instruments DSC 2910 or equivalent instrumentation. A sample with a weight between 2 and 6 mg is weighed into an open pan. This pan is then crimped and placed in the sample position in the calorimeter cell. An empty pan is placed in the reference position. The calorimeter cell is closed and a flow of nitrogen is passed through the cell. The heating program is set to heat the sample at a heating rate of 10° C./min to a temperature of approximately 100° C. When the run is completed, the data are analyzed using the DSC analysis program in the system software. The melting endotherm is integrated between baseline temperature points that are above and below the temperature range over which the endotherm is observed. The data reported are the onset temperature, peak temperature and enthalpy.

Because amorphous forms of compound 12 may be present in some samples, when an additional endotherm is observed in the DSC curves that can be due to enthalpic relaxation of the amorphous phase present, modulated DSC (MDSC) is used to confirm that the extra endotherm is not due to melting of an impurity. MDSC uses a sinusoidal or modulated change in the heating rate instead of a single linear heating rate, as used in the traditional DSC. This allows the heat flow to be separated into reversible and nonreversible components. The glass transition of amorphous material is detected in the reversible heat flow curve as a change in the baseline, due to a change of the heat capacity of the sample.

DSC data are acquired using a TA Instruments DSC Q1000. Between 2 and 6 mg of sample is weighed into an open pan. This pan is then crimped and placed in the sample position in the calorimeter cell. An empty pan is placed in the reference position. The calorimeter cell is closed and a flow of nitrogen is passed through the cell. The heating program is set to heat the sample at a heating rate of 3° C./min with a modulation period of 60 seconds and modulation amplitude of ±1° C. The final temperature is chosen to be 100° C. When a run has been completed, the data are analyzed using the DSC analysis program in the system software. The melting endotherm in the total heat flow curve is integrated between baseline temperature points that are above and below the temperature range over which the endotherm is observed. The data reported are the onset temperature, peak temperature and enthalpy. When a change of the baseline of the reversible heat flow curve is observed due to a glass transition, the data reported are the onset temperature, midpoint temperature, endset temperature and heat capacity change.

Characterization Data

FIG. 1 shows a typical X-ray powder diffraction pattern of the crystalline non-solvate form. The crystalline non-solvate form exhibits characteristic diffraction peaks corresponding to d-spacings of 4.66, 4.59, and 4.36 angstroms. The crystalline non-solvate form is further characterized by the d-spacings of 11.89, 4.02, and 3.76 angstroms. The crystalline non-solvate form is even further characterized by the d-spacings of 12.95, 7.41, and 6.51 angstroms.

FIG. 2 is a typical DSC curve of the crystalline non-solvate form of compound 12. The endotherm with an extrapolated onset temperature of 69.62° C. in FIG. 2 is due to melting (or a crystalline-amorphous phase transition).

Figure 3:
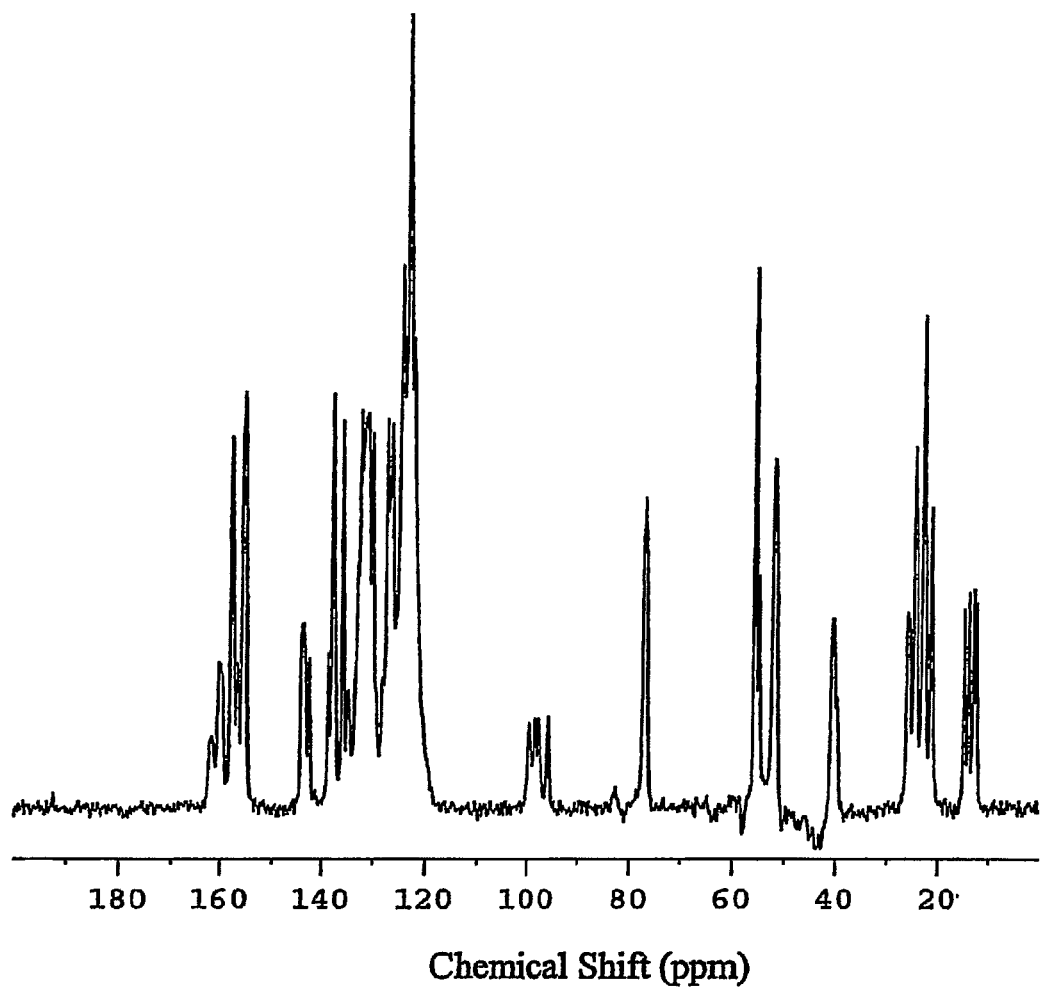
FIG. 3 is a typical carbon-13 cross-polarization magic-angle spinning (CPMAS) nuclear magnetic resonance (NMR) spectrum of the crystalline non-solvate form of compound 12.

FIG. 3 shows a typical solid-state carbon-13 CPMAS NMR spectrum of the crystalline non-solvate form of compound 12. The crystalline non-solvate form exhibits characteristic signals with chemical shift values of 123.4, 55.8, and 23.1 p.p.m. Further characteristic of the crystalline non-solvate form are the signals with chemical shift values of 124.5, 155.3, and 137.7 p.p.m. The crystalline non-solvate form is even further characterized by signals with chemical shift values of 24.8, 13.1, and 132.3 p.p.m.

Figure 4:
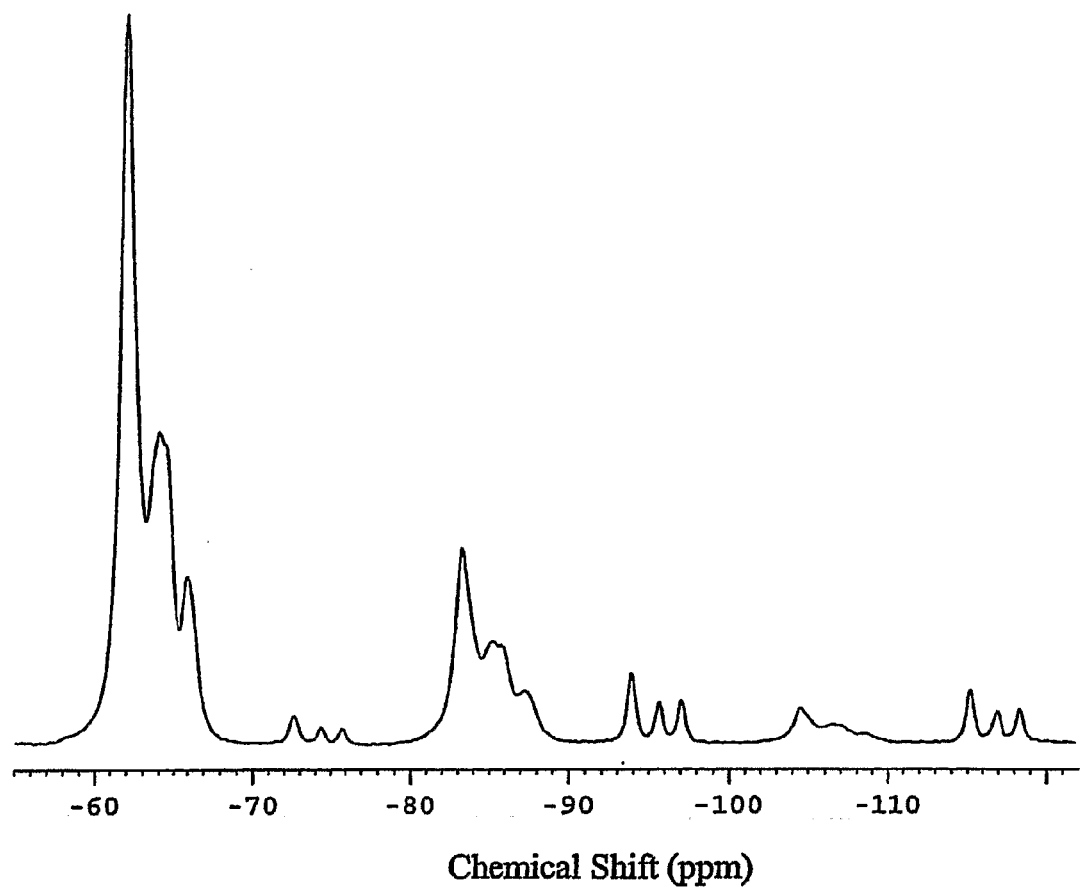
FIG. 4 is a typical fluorine-19 cross-polarization magic-angle spinning (CPMAS) nuclear magnetic resonance (NMR) spectrum of the crystalline non-solvate form of compound 12.

FIG. 4 shows a typical solid-state fluorine-19 CPMAS NMR spectrum of the crystalline non-solvate form of compound 12. The crystalline non-solvate form exhibits characteristic signals with chemical shift values of −62.1, −63.9, and −66.0 p.p.m. The crystalline non-solvate form is further characterized by signals with chemical shift values of −115.2, −116.9, and −118.3 p.p.m.

Figure 5:
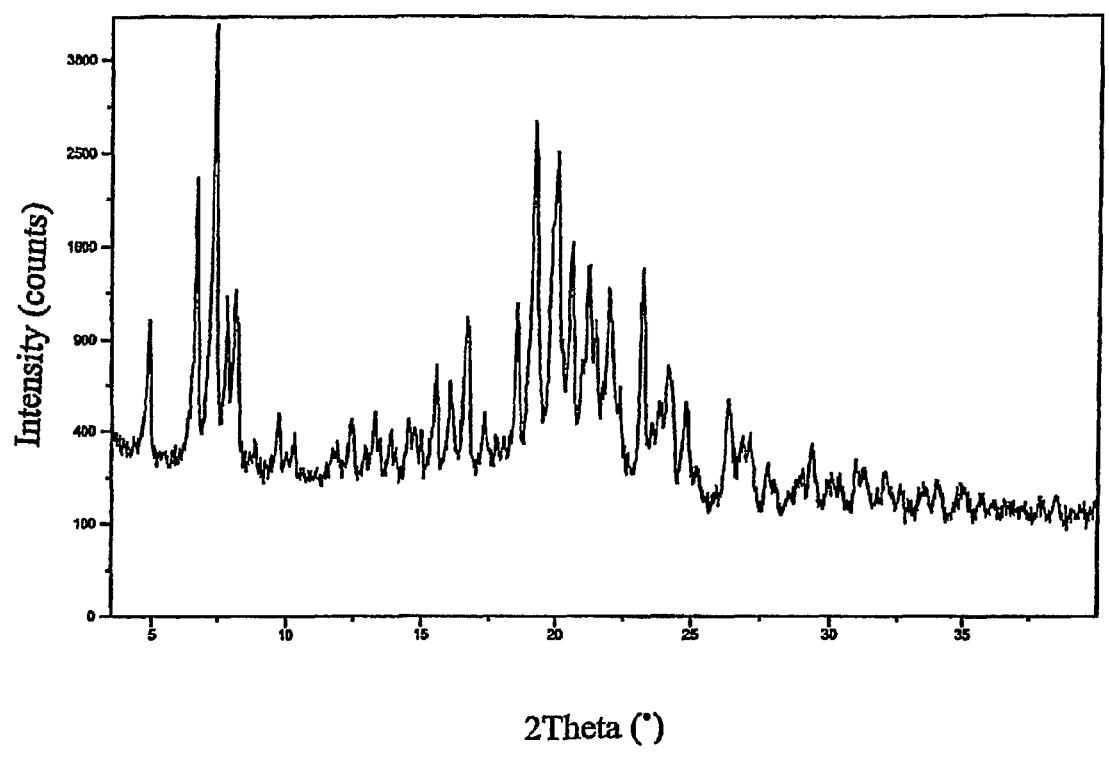
FIG. 5 is a characteristic X-ray powder diffraction pattern of the crystalline heptane solvate form of compound 12.

FIG. 5 shows a typical X-ray powder diffraction pattern of the crystalline heptane solvate form. The heptane solvate form exhibits characteristic diffraction peaks corresponding to d-spacings of 4.79, 4.62, and 4.43 angstroms. The crystalline heptane solvate form is further characterized by d-spacings of 4.20, 4.05 and 3.84 angstroms. The crystalline heptane solvate form is even further characterized by d-spacings of 13.12, 11.99, and 5.52 angstroms.

Figure 6:
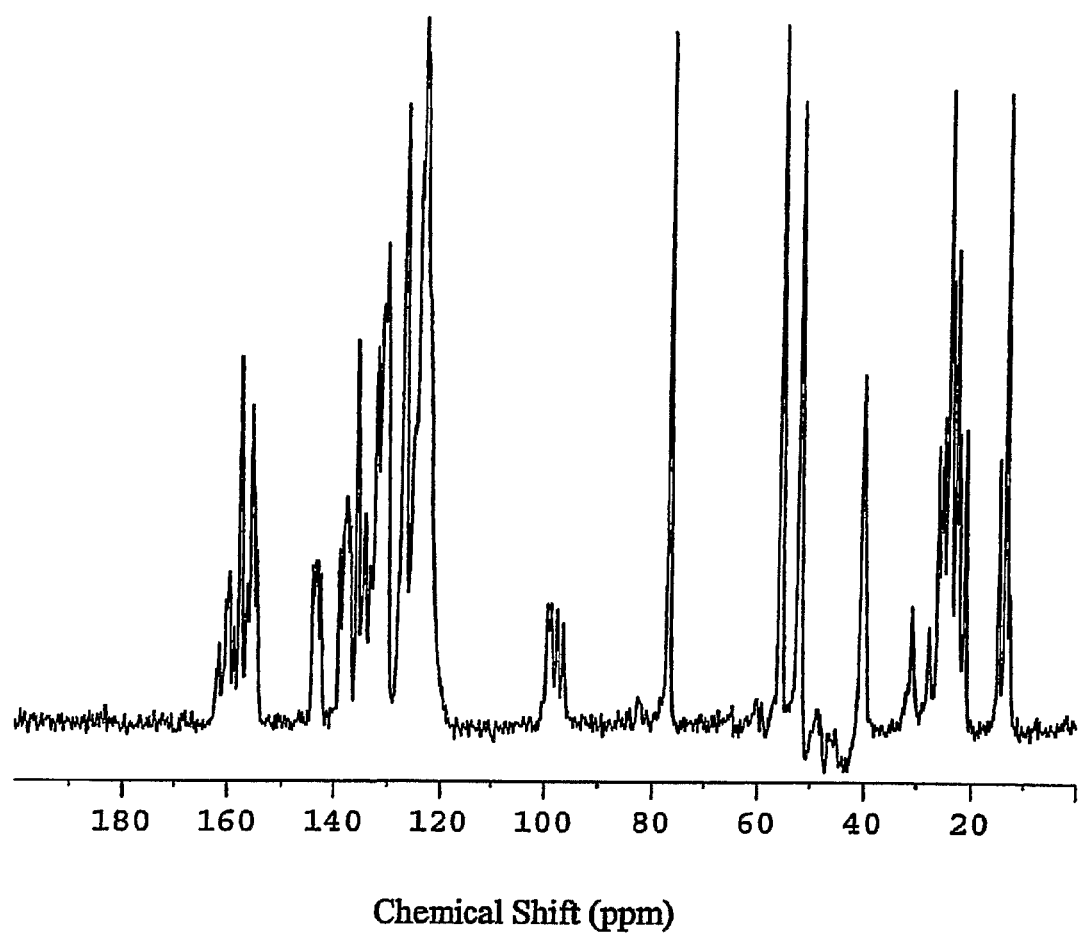
FIG. 6 is a typical carbon-13 cross-polarization magic-angle spinning (CPMAS) nuclear magnetic resonance (NMR) spectrum of the crystalline heptane solvate form of compound 12.

FIG. 6 shows a typical solid-state carbon-13 CPMAS NMR spectrum of the crystalline heptane solvate form of compound 12. The crystalline heptane solvate form exhibits characteristic signals with chemical shift values of 123.6, 55.9, and 77.1 p.p.m. Further characteristic of the crystalline heptane solvate form are the signals with chemical shift values of 24.6, 13.6, and 126.8 p.p.m. The crystalline heptane solvate form is even further characterized by signals with chemical shift values of 52.3, 130.5, and 23.2 p.p.m.

Figure 7:
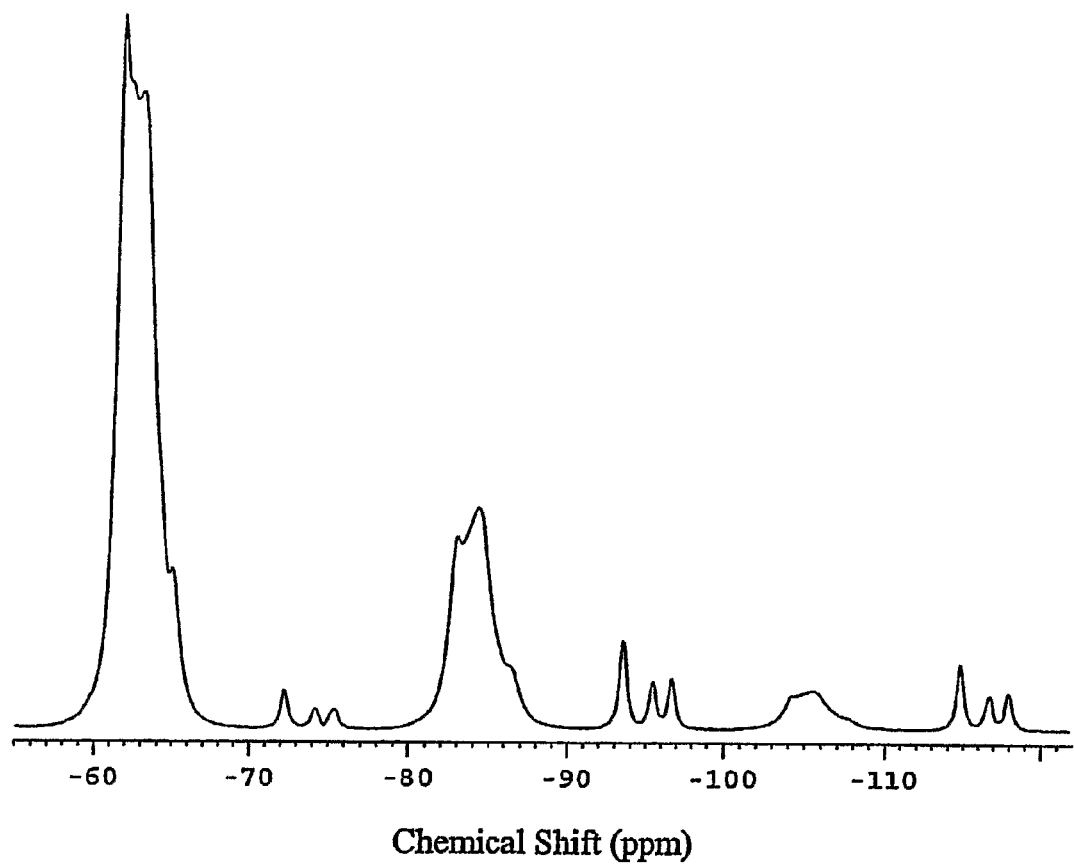
FIG. 7 is a typical fluorine-19 cross-polarization magic-angle spinning (CPMAS) nuclear magnetic resonance (NMR) spectrum of the crystalline heptane solvate form of compound 12.

FIG. 7 shows a typical solid-state fluorine-19 CPMAS NMR spectrum of the crystalline heptane solvate form of compound 12. The crystalline heptane solvate form exhibits characteristic signals with chemical shift value of −61.8, −62.9, and −65.2 p.p.m. The crystalline heptane solvate form is further characterized by signals with chemical shift values of −114.8, −117.9, and −116.7 p.p.m.

Figure 8:
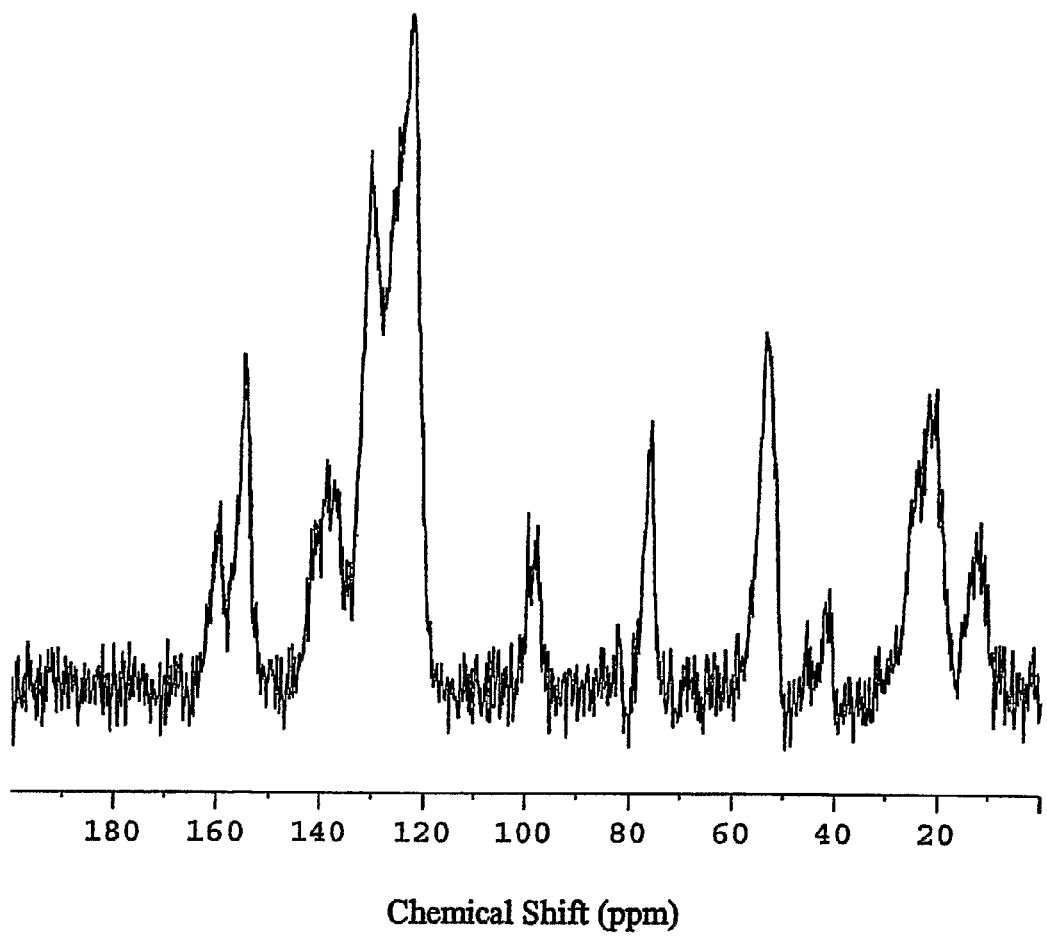
FIG. 8 is a typical carbon-13 cross-polarization magic-angle spinning (CPMAS) nuclear magnetic resonance (NMR) spectrum of the amorphous form of compound 12.

FIG. 8 shows a typical solid-state carbon-13 CPMAS NMR spectrum of the amorphous form of compound 12. The amorphous form exhibits characteristic signals with chemical shift values of 54.3, 123.5, and 155.1 p.p.m. Further characteristic of the amorphous form are the signals with chemical shift values of 22.3, 76.6, and 138.1 p.p.m. The amorphous form is even further characterized by signals with chemical shift values of 159.8, 12.3, and 98.9 p.p.m.

Figure 9:
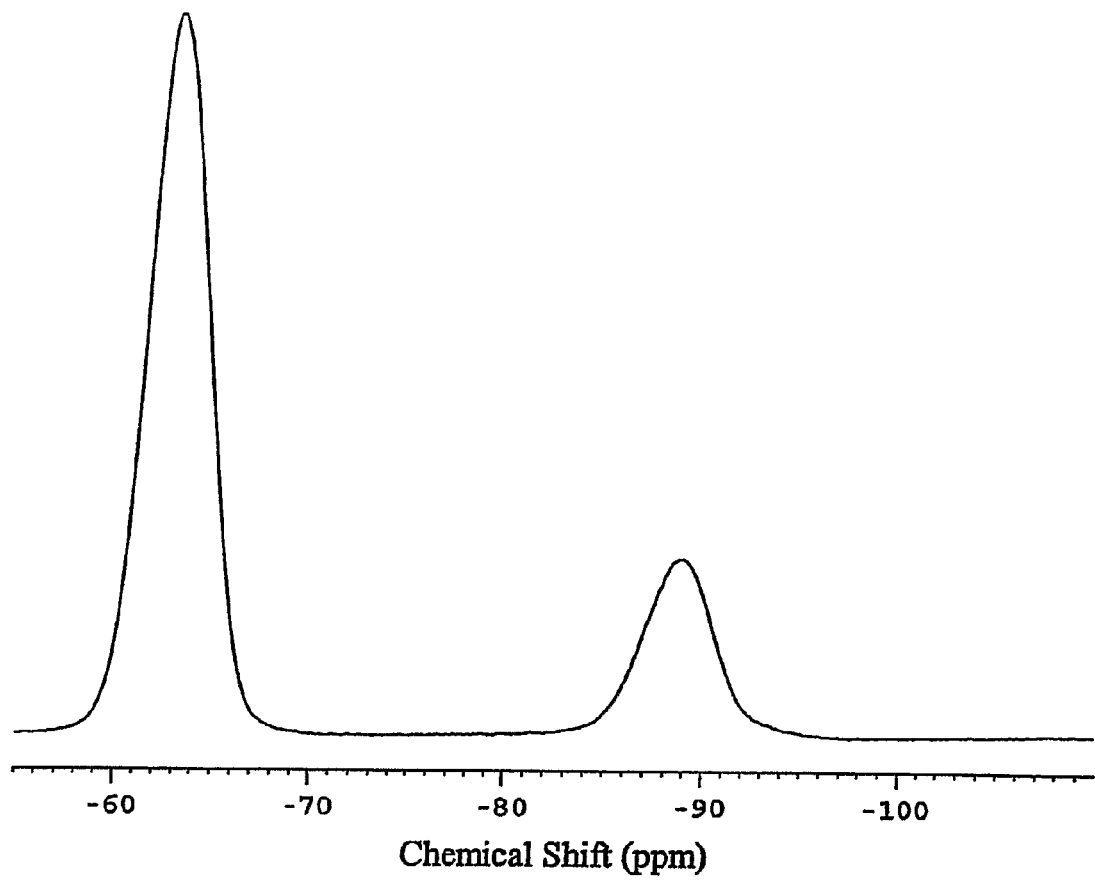
FIG. 9 is a typical fluorine-19 cross-polarization magic-angle spinning (CPMAS) nuclear magnetic resonance (NMR) spectrum of the amorphous form of compound 12.

FIG. 9 shows a typical solid-state fluorine-19 CPMAS NMR spectrum of the amorphous form of compound 12. The amorphous form exhibits a characteristic signal with chemical shift value of −63.3 p.p.m.

Figure 10:
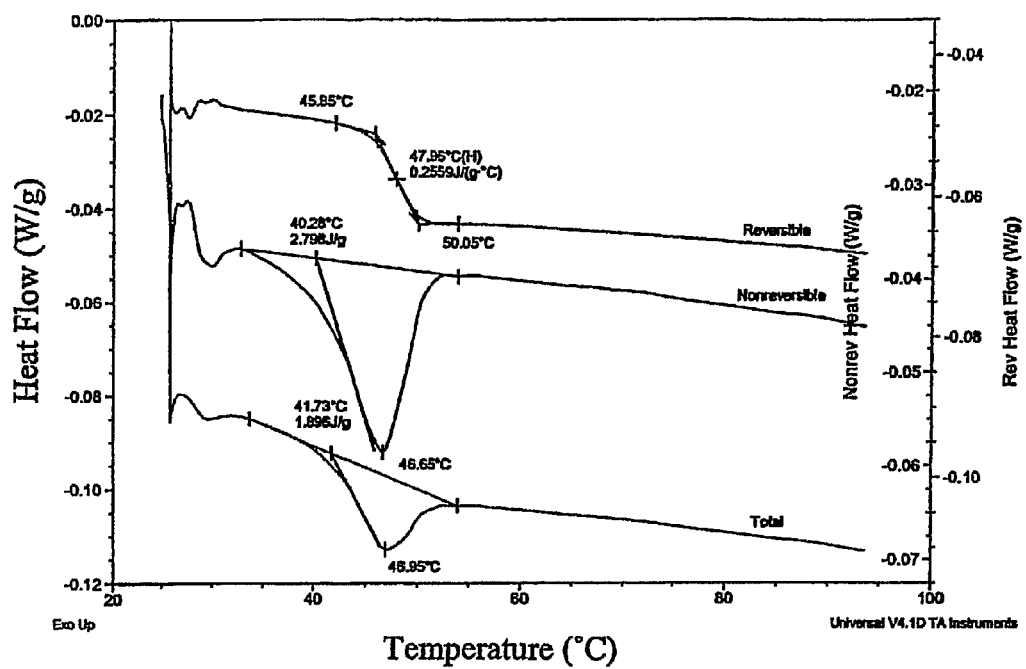
FIG. 10 is a typical modulated DSC (MDSC) curve of the amorphous form of compound 12.

FIG. 10 is a typical MDSC curve of the amorphous form of compound 12. The heat capacity change observed in the reversible heat flow curve with a midpoint temperature of 47.96° C. corresponds to the glass transition of amorphous compound 12.

Utility

The compounds and crystalline polymorphs made by the process disclosed herein are inhibitors of CETP and have utility in increasing the amount of HDL-cholesterol and reducing the amount of LDL-cholesterol in a patient, preferably a human patient. Increases of HDL and reductions of LDL are known to a practitioner in the field of medicine to be advantageous in reducing atherosclerosis and associated diseases.

The compounds synthesized by the process herein have very low solubility in aqueous environments, and are likely to be made into formulations that improve oral bioavailability compared with formulations that are conventionally made using solid active ingredients and excipients to make tablets. Crystalline products that are obtained in these preparations are readily purified, and may be formulated by dissolving them in oils and/or surfactants or dispersing them as non-crystalline dispersions in water soluble polymers, such as poly(vinylpyrrolidinone).

An exemplary formulation of the crystalline non-solvate of Compound 12 comprises a dose of 5 mg, 10 mg, 50 mg, 100 mg, or 150 mg dissolved in sufficient oil or a mixture of an oil and a surfactant to make 565 mg of solution for use in a gelatin capsule. Such doses would be administered once or twice a day. Such formulations are well known to those of skill in the art of pharmaceutical formulations.

What is claimed is:

1. A process for synthesizing a compound of formula 12:

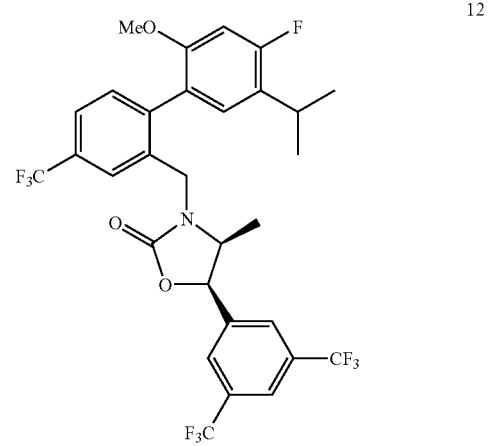

comprising the reaction of Compound 11 and Compound 7:

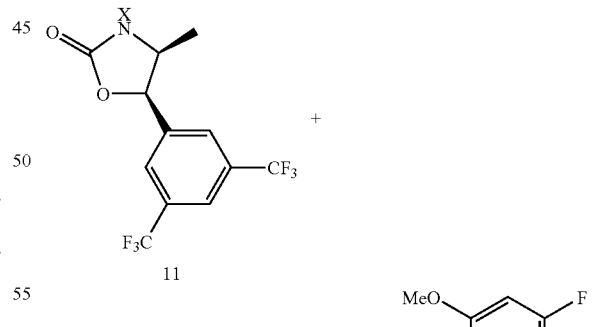

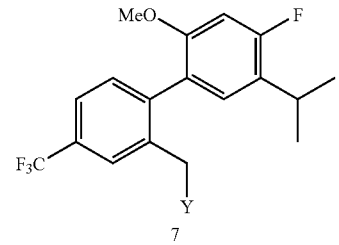

wherein X is selected from the group consisting of H, Cs, Na, K, and Li;

and Y is selected from the group consisting of Br, Cl, and I;
wherein the reaction of 11 and 7 is carried out in a solvent and at a temperature suitable for the displacement of Y by the —NX— group of the oxazolidinone ring of 11;
and when X is H, the reaction further comprises a base.

2. The process of claim 1, wherein the solvent comprises DMF, and the reaction is carried out at a temperature less than 30° C.

3. The process of claim 2, wherein X is Na; and Y is Br or Cl.

4. The compound having formula 12, characterized as being a crystalline non-solvate or a crystalline heptane solvate:

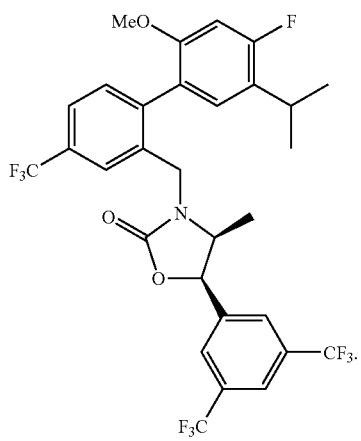

12

5. The compound of claim 4 having formula 12, characterized as being a crystalline non-solvate.

6. The compound of claim 5 having Formula 12, characterized by XRPD diffraction peaks corresponding to d-spacings of 4.66, 4.59, and 4.36 angstroms.

7. The compound of claim 5 having Formula 12, characterized by XRPD diffraction peaks corresponding to d-spacings of 11.89, 4.02, and 3.76 angstroms.

8. The compound of claim 5 having Formula 12, characterized by XRPD diffraction peaks corresponding to d-spacings of 12.95, 7.41, and 6.51 angstroms.

9. The compound of claim 5 having Formula 12, characterized by XRPD diffraction peaks corresponding to d-spacings of 4.66, 4.59, 4.36, 11.89, 4.02, 3.76, 12.95, 7.41, and 6.51 angstroms.

10. The compound of claim 5 having Formula 12, characterized by peaks in the solid-state carbon-13 CPMAS NMR spectrum having chemical shift values of 123.4, 55.8, 23.1, 124.5, 155.3, 137.7, 24.8, 13.1, and 132.3 ppm.

11. The compound of claim 5 having Formula 12, characterized by peaks in the solid-state fluorine-19 CPMAS NMR spectrum having chemical shift values of −62.1, −63.9, −66.0, −115.2, −116.9, and −118.3 ppm.

12. The compound of claim 5 having Formula 12, characterized by a DSC curve having an endotherm with an extrapolated onset temperature of 69.62° C.

13. The compound of claim 4 having formula 12, characterized as being a crystalline heptane solvate.

14. The compound of claim 13 having Formula 12, characterized by XRPD diffraction peaks corresponding to d-spacings of 4.79, 4.62, and 4.43 angstroms.

15. The compound of claim 13 having Formula 12, characterized by XRPD diffraction peaks corresponding to d-spacings of 4.20, 4.05 and 3.84 angstroms.

16. The compound of claim 13 having Formula 12, characterized by XRPD diffraction peaks corresponding to d-spacings of 13.12, 11.99, and 5.52 angstroms.

17. The compound of claim 13 having Formula 12, characterized by XRPD diffraction peaks corresponding to d-spacings of 4.79, 4.62, 4.43, 4.20, 4.05, 3.84, 13.12, 11.99, and 5.52 angstroms.

18. The compound of claim 13 having Formula 12, characterized by peaks in the solid-state carbon-13 CPMAS NMR spectrum having chemical shift values of 123.6, 55.9, 77.1, 24.6, 13.6, 126.8, 52.3, 130.5, and 23.2 ppm.

19. The compound of claim 13 having Formula 12, characterized by peaks in the solid-state fluorine-19 CPMAS NMR spectrum having chemical shift values of −61.8, −62.9, −65.2, −114.8, −117.9, and −116.7 ppm.

20. A pharmaceutical composition comprising the crystalline non-solvate form of the compound of claim 4 having Formula 12.

21. The pharmaceutical composition of claim 20, comprising a detectable amount of the compound of claim 4 having Formula 12, characterized as the crystalline non-solvate form.

22. The pharmaceutical composition of claim 20, comprising a measurable amount of the compound of claim 4 having Formula 12, characterized as the crystalline non-solvate form.

23. A method of treating atherosclerosis in a patient in need of treatment comprising the administration of a therapeutically effective amount of the compound of claim 4 having Formula 12, characterized as being a crystalline non-solvate.

24. A pharmaceutical composition comprising (a) the crystalline non-solvate form of the compound of claim 4 having Formula 12; and (b) an active pharmaceutical ingredient selected from the group consisting of a statin, a DPP-IV inhibitor, a selective PPAR-gamma partial agonist, and a CB-1 inverse agonist.

* * * * *

UNITED STATES PATENT AND TRADEMARK OFFICE
CERTIFICATE OF CORRECTION

PATENT NO. : 7,863,307 B2  Page 1 of 1
APPLICATION NO. : 11/922905
DATED : January 4, 2011
INVENTOR(S) : Ross A. Miller et al.

It is certified that error appears in the above-identified patent and that said Letters Patent is hereby corrected as shown below:

On the title page:

Insert Item -- (73) Assignee: MERCK SHARP & DOHME CORP., Rahway, NJ (US) --

Signed and Sealed this
Second Day of August, 2011

David J. Kappos
*Director of the United States Patent and Trademark Office*